United States Patent
Wei et al.

(10) Patent No.: US 7,140,730 B2
(45) Date of Patent: Nov. 28, 2006

(54) OPTICAL APPARATUS AND METHOD FOR COMPREHENSIVE EYE DIAGNOSIS

(75) Inventors: Jay Wei, Fremont, CA (US); Yonghua Zhao, Fremont, CA (US)

(73) Assignee: Optovue, Inc., Fremont, CA (US)

( * ) Notice: Subject to any disclaimer, the term of this patent is extended or adjusted under 35 U.S.C. 154(b) by 0 days.

(21) Appl. No.: 11/262,133

(22) Filed: Oct. 28, 2005

(65) Prior Publication Data

US 2006/0114411 A1    Jun. 1, 2006

Related U.S. Application Data

(60) Provisional application No. 60/626,357, filed on Nov. 8, 2004.

(51) Int. Cl.
   *A61B 3/13* (2006.01)
   *G01B 9/02* (2006.01)

(52) U.S. Cl. ............... 351/206; 351/211; 351/221; 356/450

(58) Field of Classification Search ......... 351/206, 351/211, 221, 205, 207, 208, 213, 214, 224, 351/237; 356/450, 496
See application file for complete search history.

(56) References Cited

U.S. PATENT DOCUMENTS

| 4,102,563 | A | | 7/1978 | Matsumura et al. |
| 4,421,391 | A | * | 12/1983 | Matsumura et al. ........ 351/211 |
| 5,321,501 | A | | 6/1994 | Swanson et al. |
| 5,506,634 | A | | 4/1996 | Wei et al. |
| 5,537,162 | A | | 7/1996 | Hellmuth et al. |
| 2003/0071970 | A1 | | 4/2003 | Donnerhacke et al. |

OTHER PUBLICATIONS

Parisi, V. et al., "Visual Function Correlates with Nerve Fiber Layer Thickness in Eyes Affected by Ocular Hypertension," Invest Ophthalmol Vis Sci. (1999), 40(8):1828-33.

Sabates, N., et al., "The MP-1 Microperimeter, Clinical Applications in Retinal Pathologies," Highlights of Ophthalmology, 33(4): 12-17.

* cited by examiner

Primary Examiner—Charles A Marmor, II
Assistant Examiner—John R Sanders
(74) Attorney, Agent, or Firm—Finnegan, Henderson, Farabow, Garrett & Dunner, L.L.P.

(57) ABSTRACT

An eye examination instrument is presented that can perform multiple eye tests. The instrument includes an illumination optical path and an imaging optical path, wherein a focus element in the illumination optical path is mechanically coupled to a focus element in the imaging optical path. In some embodiments, the eye examination instrument can perform a visual eye test, a fundus imaging test, and an optical coherence tomography test.

19 Claims, 4 Drawing Sheets

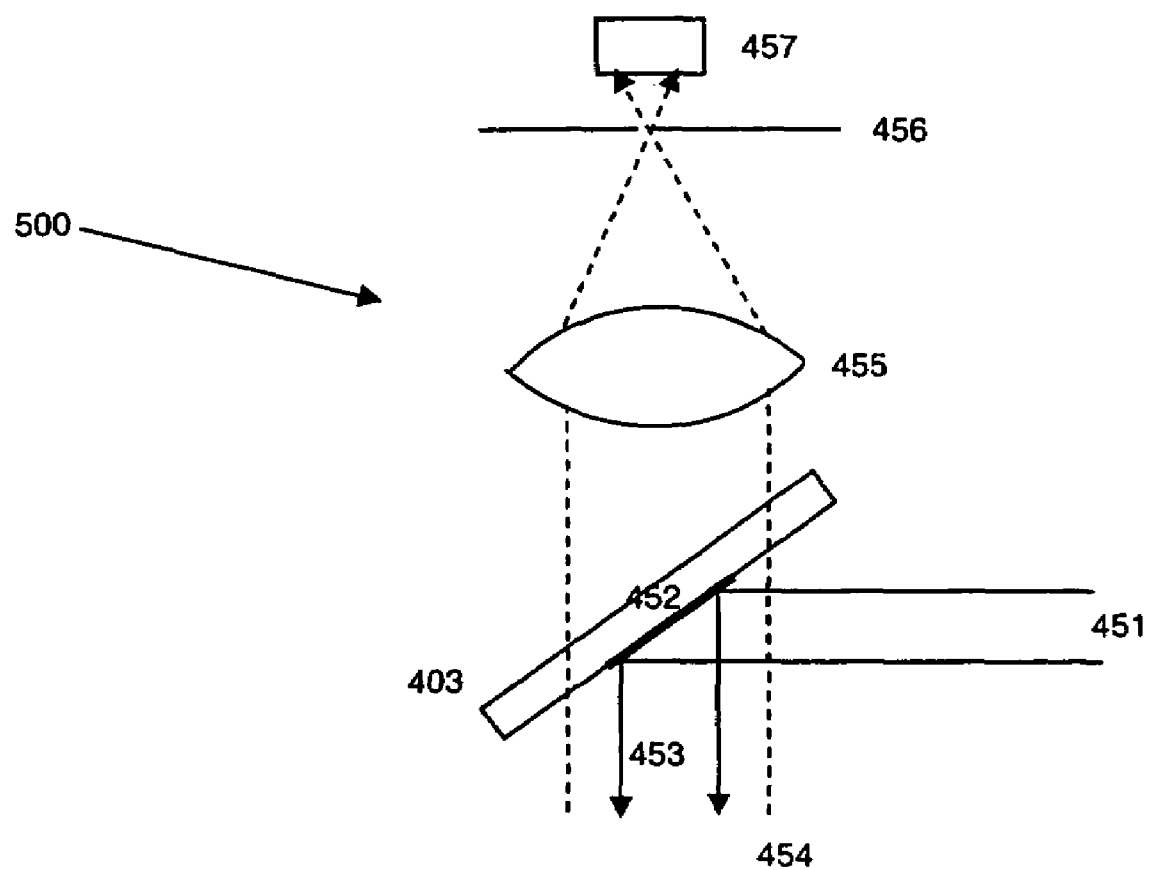

OPTICAL APPARATUS AND METHOD FOR COMPREHENSIVE EYE DIAGNOSIS

This disclosure claims priority to U.S. Provisional App. No. 60/626,357 filed on Nov. 8, 2004, by Jay Wei and Yonghua Zhao, which is herein incorporated by reference in its entirety.

BACKGROUND

1. Field of the Invention

This invention is related to optical inspection instrumentation and, in particular, to an apparatus and method that can be utilized in comprehensive eye diagnosis.

2. Discussion of Related Art

Visual field testing is a conventional clinical method utilized in the diagnosis of eye diseases that cause degradation of vision sensitivity. One of the most accepted methods utilized in the diagnosis of such diseases is the Standard Automated Perimeter (SAP) test, which tests brightness contrast sensitivity over a large visual field. There are many instruments for performing an SAP test routinely used in clinics including, for example, those produced by Carl Zeiss Meditec (Dublin, Calif.).

Typically, visual field testing utilizes functional field testing techniques. However, a functional field test technique is a functional test of vision degradation. Due to the human eye's complex multiplexing capability, the functional field test is not a sensitive measure of eye structure, which would be highly useful in the early diagnoses of such eye diseases before substantial degradation has occurred. Such structural tests include, for example, retinal image testing and optical coherence tomography.

Retinal image testing can be performed with conventional optical imaging methodology and has been routinely used in clinics for retinal structure change evaluation in addition to visual field tests. Devices such as a fundus camera or an indirect ophthalmoscope are routinely used for such testing. The retinal image provides valuable information that clinicians can utilize to diagnosis eye diseases. However, only qualitative interpretation of eye structure changes from the retinal photographs can be observed by highly experienced clinicians.

Optical Coherence Tomography (OCT) is a new imaging modality that has been used for non-invasive human eye retinal imaging. The cross sectional retinal image allows a clinician to quantitatively evaluate the retinal nerve layer and retinal thickness. Valuable clinical information can be extracted for early diagnosis of eye diseases, such as Glaucoma. However, at the end stage of the disease, when the patient s lose most of their Retinal Nerve Fiber Layer (RNFL), the OCT imaging method has certain technical difficulties in accurately measuring the RNFL. Therefore, it is difficult to follow the progression of diseases, such as glaucoma, with OCT techniques.

In light of the above-mentioned disadvantages over individual examination methods, clinicians need to have multiple examination results in comprehensive eye examinations to accurately assess the condition of the eye and detect diseases before patients exhibit overt symptoms. Currently, these exams are done separately on different instruments. At most, two methods are combined, as in, for example, the Microperimeter produced by Nidek Corp, Japan. Currently, there is no apparatus that is able to integrate a visual field test and OCT together. Therefore, there is a need for instruments for eye examination that allow a clinical practitioner to fully evaluate the structure of the eye in order to help diagnose and treat eye disease.

SUMMARY

In accordance with the present invention, an optical examination instrument is presented that allows for OCT scanning, visual field testing, and fundus imaging. An apparatus for performing eye examinations according to some embodiments of the present invention includes an scanning optical path, the scanning optical path including a scan beam focus adjustment group, a first lens coupled to receive the scan beam from the scan beam focus adjustment group, and a scanning galvanometer coupled to receive light from the first lens; an imaging optical path, the imaging optical path including a second lens, a retina image focus adjustment group that receives light from the second lens, and an imaging device; a beam splitter that merges the scanning optical path with the imaging optical path; and an ocular lens that focuses light onto a pupil of an eye, wherein the scan beam focus adjustment group and the retina adjustment focus adjustment group are mechanically coupled to a single focus adjustment. An optical coherence tomography scan can be performed utilizing the scanning optical path and the imaging optical path. In some embodiments, the optical coherence tomography scan can be performed with no vignetting, without dilating the pupil.

In some embodiments, the apparatus includes an illumination device and a second beam splitter coupled between the retina image focus adjustment group and the imaging device, the second beam splitter merging light from the illumination device into the imaging optical path. A visual field test can be performed utilizing the illumination device. In some embodiments, at least one light source and a spatial beam splitter, wherein light from the at least one light source is coupled into the imaging optical path by the spatial beam splitter, the light from the at least one light source providing background lighting for the visual field test. In some embodiments, the illumination device is utilized to provide an image on which a patient can fixate during an eye examination. In some embodiments, the illumination device is a device selected from a group consisting of a CRT display, a LCD display, a LED array, or a single light source that is spatially movable.

In some embodiments, the apparatus can include at least one light source and a spatial beam splitter, wherein light from the at least one light source is coupled into the imaging optical path by the spatial beam splitter. A fundus imaging test can be performed with the imaging optical path utilizing light from the at least one light source. In some embodiments, a pupil mask can be coupled between the at least one light source and the spatial beam splitter, wherein the pupil mask is conjugated onto a pupil.

In some embodiments, the scan beam adjustment group includes a beam folding mirror, a scanning mirror, and a lens. In some embodiments, the beam folding mirror includes a reflection region and a transmission region, the reflection region reflects substantially all of an input beam. In some embodiments, a confocal module can be coupled to detect light that was reflected from an eye, transmitted through the beam folding mirror. In some embodiments, the confocal module controls the single focus adjustment.

In some embodiments, an eye examination apparatus according to the present invention can include means for performing an optical coherence tomography scan on an eye; means for performing a visual field test; means for obtaining a fundus image; and means for focusing with a single focus adjustment. In some embodiments, the apparatus can include confocal adjustment means for automatically adjusting the single focus adjustment. In some embodiments, the apparatus can include means for obtaining a retinal scan. In some embodiments, the means for performing an optical coherence tomography scan without vignetting.

These and other embodiments are further discussed below with respect to the following figures.

BRIEF DESCRIPTION OF THE DRAWINGS

FIG. 5 shows an embodiment of the present invention that includes a trace of the scan beam.

In the figures, elements having the same designation have the same or similar functions.

DETAILED DESCRIPTION

In accordance with the current invention, an optical apparatus for diagnosis of eye diseases is presented. Some embodiments of optical scanner according to the present invention can be used for non-invasive retinal scanning, retinal imaging with an optical imaging system, and human visual field testing with an optical illumination system. Some embodiments of the current invention are further related to the method for a comprehensive eye exam related to eye diseases such as, for example, glaucoma.

Figure 1:
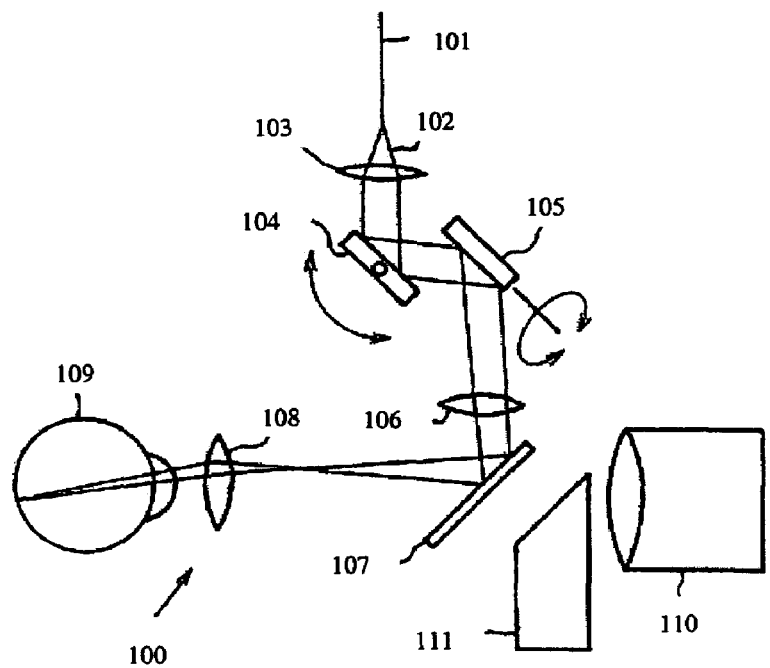
FIG. 1 shows a conventional OCT apparatus with a slit-lamp optical imaging unit.

FIG. 1 illustrates an OCT scan unit 100 that was described in U.S. Pat. No. 5,537,162, "Method and Apparatus for Optical Coherence Tomographic Fundus Imaging Without Vignetting," issued on Jul. 16, 1996. As shown in FIG. 1, light from optical fiber 101 is collimated by lens 103 and coupled into paired galvanometers 104 and 105. Together, galvanometers 104 and 105 can scan beam 102 from optical fiber 101 in two orthogonal directions, which allows scanning in any arbitrary pattern on eye 109. From galvanometer 105, light is coupled into focusing lens 106. Dichroic beam splitter 107 directs the light from focusing lens 106 into ocular lens 108, where the light is focused onto the retina of eye 109. Focusing lens 106 and ocular lens 108 form an optical relay system so that the sample beam located in the middle distance of galvanometers 104 and 105 is imaged into the entrance pupil of eye 109 and, as a result, vignetting is minimized at small scan angle.

OCT scan unit 100 is coupled to a slit-lamp optical image unit 110 and illumination unit 111. As such, an image of the fundus of eye 109 is obtained in optical image unit 110 with light from illumination unit 111.

However, scanner 100 suffers several disadvantages. First, the refractive error in eye 109 varies, typically, within a range of about ±20 diopters. Therefore, there is a need to focus the sample beam and the imaging optics of illumination unit 111 to compensate for this error. However, focusing lens 106 and imaging optics 110 are fixed and therefore focusing is accomplished entirely by moving ocular lens 108. The image from galvanometer 105 and of illumination unit 111 both move when lens 108 is moved. Illumination unit 111 usually includes a very bright light source for fundus imaging because the fundus of eye 109 usually has a low reflectivity. Therefore, adjustments must be made to keep backreflections from the cornea and from ocular lens 108 out of the observation path of image unit 110. To prevent the reflection of the scan beam back into scan unit 100, the scan beam can be directed off-center to the ocular lens and pupil of eye 109. However, these off-center adjustments cause both astigmatism and vignetting.

Figure 2:
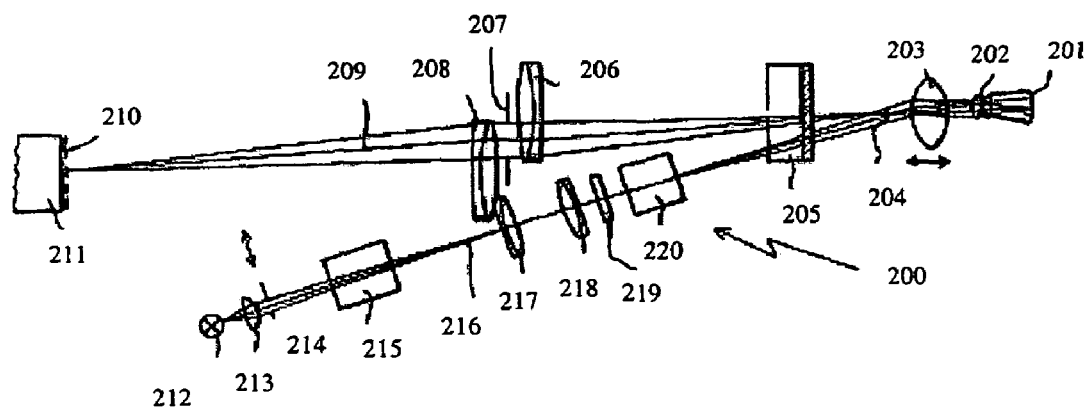
FIG. 2 shows another conventional optical inspection instrument that uses a slit-lamp design principle

FIG. 2 illustrates another conventional example scan unit 200 that utilizes OCT. Scan unit 200 utilizes a slit-lamp principle. As shown in FIG. 2, an illumination path includes light source 212, condenser lens 213, stop aperture 214, a lens system having folding glass prisms 215 and 220, relay lenses 217 and 218, and a color filter 219. Light beam 216 is directed and focused on lens 203 through beam splitter 205. Light from the illumination path is directed onto ocular lens 203 and eye pupil 202 for focusing onto retina 201. Reflected light from retina 201 is collected by ocular lens 203 and passes through beam splitter 205 into the imaging path. The imaging path includes a lens system such as lens 206, stop aperture 207, and lens 208. Imaging beam 209 is thereby focused onto image plane 210 on CCD camera 211.

As shown in FIG. 2, the combined optical path (including beam 216 and 209) is off centered on ocular lens 203 and on eye pupil 202. In such an arrangement the unwanted reflection of the illumination from ocular lens and cornea can be substantially eliminated. The scan beam path, a similar optical configuration as shown in FIG. 1 but not shown in FIG. 2, can be combined through beamsplitter 205 on to the ocular lens and eye. Due to the de-center of the optical paths, residual optical aberration always exists. Specifically, the chromatic aberration becomes a major concern when a high resolution OCT system demands an optical performance over a much broader spectrum range than can be accomplished with conventional components.

Figure 3:
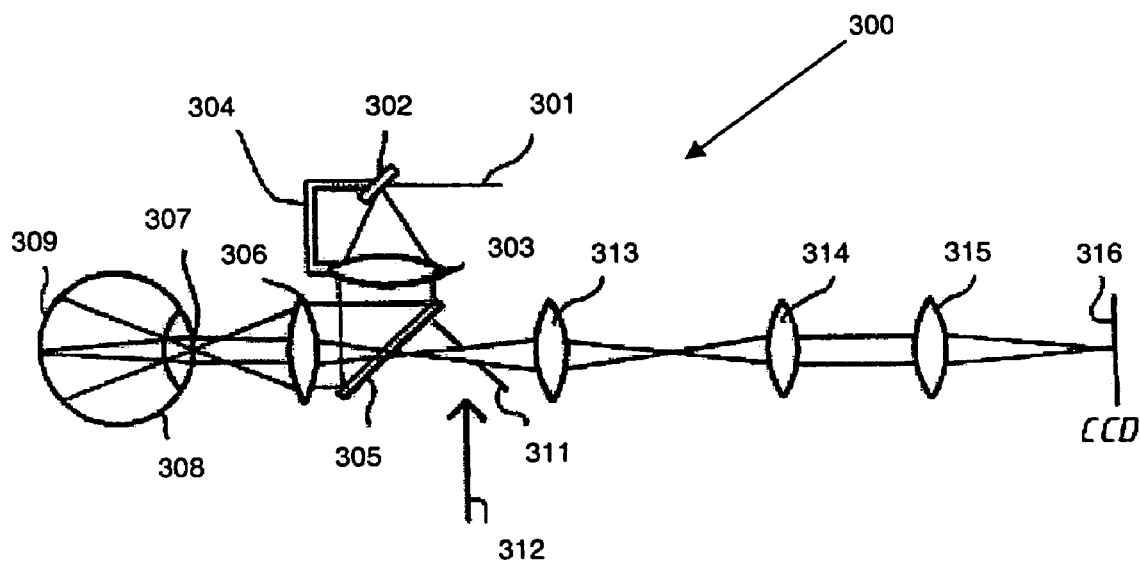
FIG. 3 shows a conventional optical inspection instrument that uses a fundus camera design.

FIG. 3 illustrates a conventional optical system 300 that is centered as in a fundus camera configuration. As shown in FIG. 3, scan beam 301 is directed by a scanner mirror 302 and scanning lens 303 into the image path by a beamsplitter 305. The optical image path, consisting of elements 306 to 316 (specifically ocular lens 306, focusing lenses 313, 314, and 315, and imaging device 316), is configured like a fundus camera. The eye pupil 307 is imaged to a spatial beamsplitter 311, which can be a mirror with a hole in the center, by ocular lens 306. Lens 313 images the intermediate image of the retina, an airy image close to the back focal plane of lens 306, to the front focal plane of lens 314. The retinal image is then imaged on to an image device 316, which can be a CCD camera or film camera, for example, by lenses 314 and 315. Lens 314 can be moveable to compensate for any refraction error of the patient's eye 308. The scan beam module 304, which includes scanning galvanometer 302 with lens 303, is also moveable to compensate the refraction error of the patient's eye 308.

However, one major disadvantage in scan system 300 shown in FIG. 3 is that scanning galvanometer 302, the pivot point of the scanning beam, is not image conjugated on pupil 307 of eye 308. When exercising a large scan angle in optical system 300, some portion of the beam will be vignetted by patient's pupil 307. So, a large pupil is required to prevent this vignetting problem. This requirement is especially disadvantageous for glaucoma patients because the use of mydriatic eye drops to dilate the eye pupil could cause clinic complications.

The illumination path and imaging path optics such as that shown in FIG. 3 are well known in the ophthalmic imaging field and is a commercially available device. Such a fundus camera has been widely used clinically today. Recently, Nidek Corporation has integrated the visual field test into such a fundus camera.

As a result, each of the systems that are typically utilized in clinics for the diagnosis of eye diseases that cause visual degradation are not ideal. The optical systems illustrated in FIGS. 1 and 2 both use off-axis optical systems. The chromatic aberration of the OCT scan beam, therefore, is significant. Although sufficient for a low resolution OCT system with a narrow spectral bandwidth light source, such chromatic aberration is highly detrimental in high resolution OCT system where the scan beam light source has a broad spectral bandwidth. When a high resolution OCT system is coupled with the above off-centered optical systems, the chromatic aberration will cause the spectral bandwidth to be degraded in the detector optical path. As a result, high resolution OCT can not be achieved. Furthermore, because the operator has to adjust the ocular lens, which is the lens closest to the patient's eye, there is always a concern that the lens will accidentally contact the patient's eye during adjustment. To avoid a scan beam vignetting problem for a large scan field, the optical system illustrated in FIG. 3 requires dilation of the patient's pupil. Such pupil dilation is contraindicated with many optical diseases.

Figure 4:
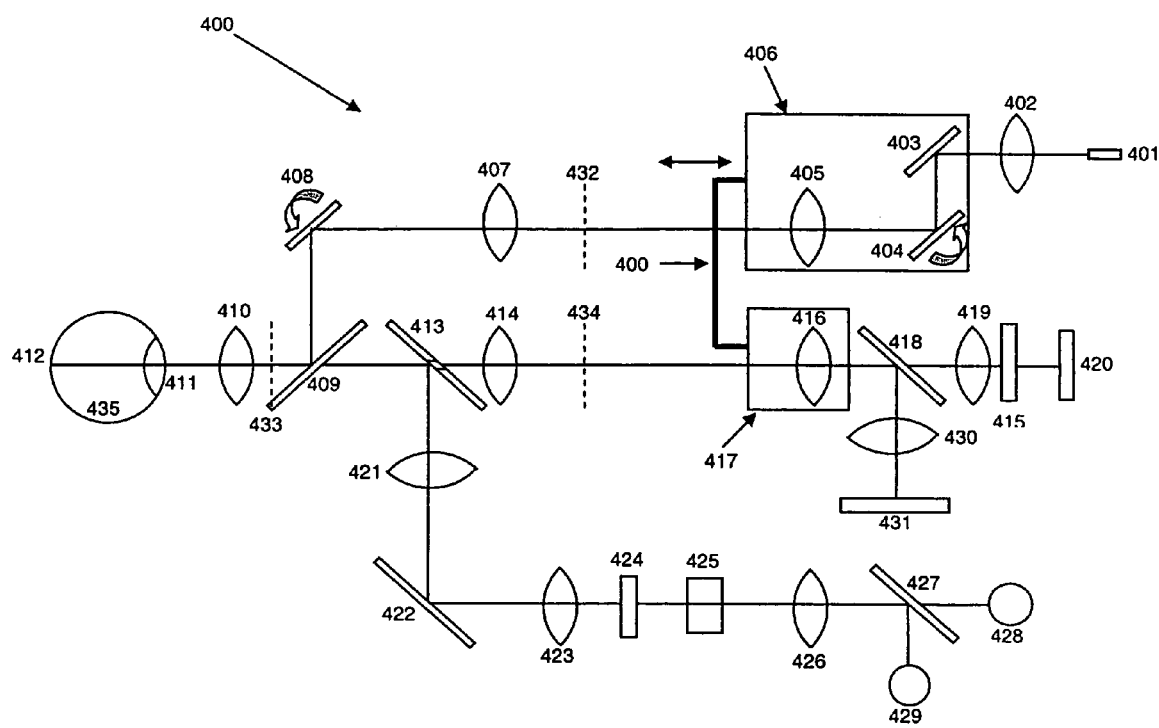
FIG. 4 shows an optical instrument according to some embodiments of the present invention.

FIG. 4 illustrates a scanning system 400 according to some embodiments of the present invention. Embodiments of scanning system 400 overcome the above-mentioned instrument disadvantages and also provide an integrated eye examination set up and method. In FIG. 4, an optical element that is drawn and described as a lens can be any lens system that performs the described task.

As shown in FIG. 4, OCT beam 401 is collimated by lens 402, folded by mirror 403, scanned by scanner mirror 404, and focused on the intermediate image plane 432 by lens 405. Image plane 432 is relayed on to another intermediate image plane 433 by lens 407, scanning mirror 408, and dichroic beam splitter 409. Image plane 433 is conjugated (i.e., imaged) to retina 412 through ocular lens 410 and eye 435. The pupil 411 of eye 435 is conjugated on the scanner mirror 408 by lens 410 and then relayed to scan mirror 404 by lenses 407 and 405. It is worth noting that in this configuration, the beam scanning pivot position on both scan directions are all conjugated on pupil 411 of eye 435. So, the pupil size need not be increased with increased scan angle. Therefore, no beam vignetting occurs on patients with small pupils.

In the imaging path, retina 412 is imaged onto an image plane 433 by eye 435 and lens 410, and relayed to image plane 434 by lens 414. Finally, the image plane 434 is relayed onto an image device 420 by lenses 416 and 419. Image device 420 can, for example, be a CCD or film camera. An image originating at illumination device 431 can be relayed to image plane 434 by lenses 416 and 430 and beam splitter 418. Illumination device 431 can be realized with numerous methods, for example, a graphic display device such as, but not limited to, a CRT or LCD, a LED array, or a single light source that can be moved around the image plane with mechanic devices, etc. Beamsplitter 418 splits these two optical paths (that of an image being transmitted to image device 420 and that of an image being generated by imaging device 431) with a dichroic beamsplitter coating. A coating for beam splitter 418 can depend on the specific clinical application. For example, in a blue-yellow perimetry, the coating can reflect the blue light spectrum and transmit wavelengths longer than the blue wavelengths. As a result, the reflection of blue wavelength from the lenses 416, 414, 410 and eye 435 will not be able to reach the imaging device 420. In some embodiments, a filter 415 placed in front of image device 420 can be used to block the reflection of scan beam 401 from lenses 410 and eye 435.

In some embodiments, scan beam focus adjustment group 406 (which includes beam folding mirror 403, scanning mirror 404, and focusing lens 405) and retina image focus group 417 (which includes lens 416) can be mechanically coupled together with a fixed gear ratio that depends on the optical design to compensate for the refraction error of the patient's eye under test. It is advantageous to have single focusing adjustment knob to focus both the scan beam and retina image simultaneously.

Additionally, scan beam 401 is combined into the retina image path in front of beamsplitter 413 by beam splitter 409. Beam splitter 413 can be a spatial splitter that has a small hole that is precision aligned with the optical axis of the imaging beam path.

In the illumination path, light source 428 is imaged onto the pupil mask 425, which can have a ring-shape open area. The illuminated ring is conjugated onto beamsplitter 413 and then conjugated onto eye pupil 411 by lens 410. The reflection of the illumination from lens 410 is blocked by a small opaque area on mask 424, which is conjugated on the lens surfaces 410 by lens 423 and lens 421. A different light source, source 429, can be combined into the illumination path by beamsplitter 427.

In the embodiment of scanner 400 shown in FIG. 4, a visual field test can be realized by using illumination device 431 to generate the visual field test stimulus. Light source 428 can be utilized to provide background illumination. Illumination device 431 can also serve as an internal fixation device for patients to stabilize their eye movement during the examination. In addition to the visual field test, an OCT scan can be performed with scanning optical path optics. Further, fundus imaging can be performed with light sources 428 and 429 and imaging device 420. In some embodiments, other optical tests, such as, for example, confocal retinal imaging, can also be performed on eye 435.

It is highly advantageous to have an integrated scanner such as scanner 400 that can perform a visual field test, an OCT scan, fundus imaging, and confocal retinal imaging. Through registration of anatomic features and functionality, the patient's pathology can be better comprehended by the clinician if all three tests are performed on the same system.

FIG. 5 illustrates an embodiment of a confocal module 500 that can be coupled to scan beam focusing module 406 illustrated in FIG. 6. As shown in FIG. 5, OCT beam folding mirror 403 can have a small reflection region 452 that reflects a majority of OCT beam 401 into the illumination beam path as described above. The OCT beam reflected from retina 412 has a larger beam size than the original incident beam due to the scattering of the retina tissue of retina 412. As shown in FIG. 5, illumination beam 401 has a beam width 451 that is reflected by region 452 into width 453. The portion of the reflected beam that is larger than region 452 will transmit through folding mirror 403 and can be focused into a small aperture 456 by lens 455 and collected by a photo sensor 457. Confocal module 500 can be used to detect whether the OCT beam is on focus on retina 412. Like a scanning laser confocal ophthalmoscope (SLO), the intensity of the light detect by photo sensor 457 is related to the focus of beam 401 on retina 412. An output signal from detector 457, then, can be utilized in an autofocus circuit. It is advantageous to use this signal to simulate the scan beam trace on the retina for alignment and focusing of the scan beam.

The above example embodiments are examples only of the invention. The invention is not limited by the above example embodiments. One skilled in the art will recognize modifications of these embodiments or alternative embodiments that are intended to be within the spirit and scope of this disclosure. As such, the invention is limited only by the following claims.

What is claimed is:

1. An apparatus for performing eye examinations, comprising:
   a scanning optical path including a scan beam focus adjustment group, a first lens coupled to receive the scan beam from the scan beam focus adjustment group, and a scanning galvanometer coupled to receive light from the first lens;
   an imaging optical path including a second lens, a retina image focus adjustment group that receives light from the second lens, and an imaging device;
   a beam splitter that merges the scanning optical path with the imaging optical path; and
   an ocular lens that focuses light into a pupil of an eye,
   wherein the scan beam focus adjustment group and the retina image focus adjustment group are mechanically coupled to a single focus adjustment.

2. The apparatus of claim 1, wherein an optical coherence tomography scan can be performed utilizing the scanning optical path and the imaging optical path.

3. The apparatus of claim 2, wherein the optical coherence tomography scan can be performed with no vignetting without dilating a pupil.

4. The apparatus of claim 1, further including an illumination device and a second beam splitter coupled between the retina image focus adjustment group and the imaging device, the second beam splitter merging light from the illumination device into the imaging optical path.

5. The apparatus of claim 4, wherein a visual field test can be performed utilizing the illumination device.

6. The apparatus of claim 5, further including at least one light source and a spatial beam splitter, wherein light from the at least one light source is coupled into the imaging optical path by the spatial beam splitter, the light from the at least one light source providing background lighting for the visual field test.

7. The apparatus of claim 4, wherein the illumination device is utilized to provide an image on which a patient can fixate during an eye examination.

8. The apparatus of claim 4, wherein the illumination device is a device selected from a group consisting of a CRT display, a LCD display, a LED array, or a single light source that is spatially movable.

9. The apparatus of claim 1, further including at least one light source and a spatial beam splitter, wherein light from the at least one light source is coupled into the imaging optical path by the spatial beam splitter.

10. The apparatus of claim 9, wherein a fundus imaging test can be performed with the imaging optical path utilizing light from the at least one light source.

11. The apparatus of claim 9, further including a pupil mask coupled between the at least one light source and the spatial beam splitter, wherein the pupil mask is conjugated onto a pupil.

12. The apparatus of claim 1, wherein the scan beam adjustment group includes a beam folding mirror, a scanning mirror, and a lens.

13. The apparatus of claim 12, wherein the beam folding mirror includes a reflection region and a transmission region, the reflection region reflects substantially all of an input beam.

14. The apparatus of claim 13, further including a confocal module coupled to detect light that was reflected from an eye, transmitted through the beam folding mirror.

15. The apparatus of claim 14, wherein the confocal module controls the single focus adjustment.

16. An eye examination apparatus, comprising:
    means for performing an optical coherence tomography scan on an eye;
    means for performing a visual field test;
    means for obtaining a fundus image;
    means for focusing with a single focus adjustment; and
    means for performimg confocal fundus imaging.

17. The apparatus of claim 16, further including
    confocal adjustment means for automatically adjusting the single focus adjustment.

18. The apparatus of claim 16, further including
    means for obtaining a retinal scan.

19. The apparatus of claim 16, wherein the means for performing an optical coherence tomography scan without vignetting.

* * * * *

UNITED STATES PATENT AND TRADEMARK OFFICE
CERTIFICATE OF CORRECTION

PATENT NO.         : 7,140,730 B2
APPLICATION NO.    : 11/262133
DATED              : November 28, 2006
INVENTOR(S)        : Jay Wei and Yonghua Zhao Page 1 of 1

It is certified that error appears in the above-identified patent and that said Letters Patent is hereby corrected as shown below:

In Claim 16, column 8, line 38, please change "performimg" to --performing--.

Signed and Sealed this
Twentieth Day of March, 2012

David J. Kappos
*Director of the United States Patent and Trademark Office*